US012605146B2

(12) United States Patent
Ji et al.

(10) Patent No.: US 12,605,146 B2
(45) Date of Patent: Apr. 21, 2026

(54) SYSTEM AND METHOD FOR CONTRAST ENHANCED ULTRASOUND QUANTIFICATION IMAGING

(71) Applicant: SHENZHEN MINDRAY BIO-MEDICAL ELECTRONICS CO., LTD., Shenzhen (CN)

(72) Inventors: Ting-lan Ji, San Jose, CA (US); Zhaoling Lu, San Jose, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 390 days.

(21) Appl. No.: 16/853,603

(22) Filed: Apr. 20, 2020

(65) Prior Publication Data

US 2021/0321988 A1 Oct. 21, 2021

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/0891* (2013.01); *A61B 8/481* (2013.01);
(Continued)

(58) Field of Classification Search
CPC ..... A61B 8/5207; A61B 8/0891; A61B 8/481; A61B 8/5269; A61B 8/5292; A61B 8/06;
(Continued)

(56) References Cited

U.S. PATENT DOCUMENTS 5,743,266 A * 4/1998 Levene ................... A61B 8/06
600/458
2009/0324030 A1* 12/2009 Frinking ................. A61B 8/06
382/128
(Continued)

OTHER PUBLICATIONS

Halmann et al., Digital Subtraction Myocardial Contrast Echocardiography: Design and Application of a New Analysis Program for Myocardial Perfusion Imaging, published by the Journal of the American Society of Echocardiography, Jul.-Aug. 1994, pp. 355-362 (Year: 1994).*

*Primary Examiner* — Alexei Bykhovski
(74) *Attorney, Agent, or Firm* — Sheppard Mullin Richter & Hampton LLP

(57) ABSTRACT

Methods, systems, and apparatus, including computer programs encoded on computer storage media, for contrast enhanced ultrasound quantification imaging are provided. One of the methods includes: obtaining, for each location in a region of interest, a time-dependent ultrasound signal with respect to the region of interest for a time period; setting, for the each location, a global threshold for the obtained time-dependent ultrasound signal; determining, for the each location, a relative time instant that the time-dependent ultrasound signal reaches the global threshold; and generating a structural image of the region of interest based at least on the determined relative time instant of the each location, wherein the generated structural image displays different time instants that ultrasound signals corresponding to different locations in the region of interest reach the global threshold.

14 Claims, 9 Drawing Sheets

(51) Int. Cl.

| | |
|---|---|
| *G06T 7/00* | (2017.01) |
| *G06T 7/11* | (2017.01) |
| *G06T 11/00* | (2006.01) |
| *G16H 30/40* | (2018.01) |

(52) U.S. Cl.
CPC .......... *A61B 8/5269* (2013.01); *A61B 8/5292* (2013.01); *G06T 7/0012* (2013.01); *G06T 7/11* (2017.01); *G06T 11/001* (2013.01); *G16H 30/40* (2018.01); *G06T 2207/10132* (2013.01); *G06T 2207/30104* (2013.01)

(58) Field of Classification Search
CPC ....... A61B 8/469; A61B 8/463; A61B 8/5223; A61B 8/52; G06T 7/0012; G06T 7/11; G06T 11/001; G06T 2207/10132; G06T 2207/30104; G06T 7/0016; G06T 2207/10016; G06T 11/40; G06T 5/002;

G06T 2207/30101; G16H 30/40; G16H 40/63; G16H 50/20
See application file for complete search history.

(56) References Cited

U.S. PATENT DOCUMENTS

| | | | | |
|---|---|---|---|---|
| 2011/0213244 | A1* | 9/2011 | Frinking ................ | A61B 5/055 |
| | | | | 600/431 |
| 2011/0245675 | A1* | 10/2011 | Yoshida ................. | A61B 8/466 |
| | | | | 600/443 |
| 2014/0336513 | A1 | 11/2014 | Sang et al. | |
| 2016/0174934 | A1 | 6/2016 | Cong et al. | |
| 2017/0049416 | A1* | 2/2017 | Azar .................... | A61B 8/4483 |
| 2019/0290210 | A1 | 9/2019 | Mclaughlin | |
| 2020/0077982 | A1* | 3/2020 | Duncan .................. | A61B 8/481 |
| 2020/0357117 | A1* | 11/2020 | Lyman .................. | G16H 50/20 |

* cited by examiner

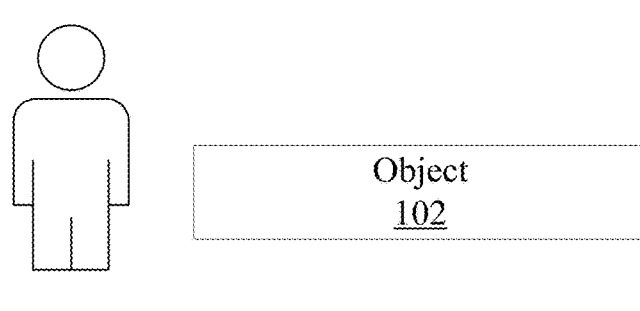
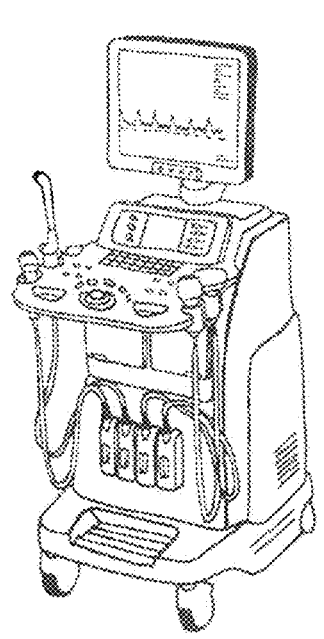
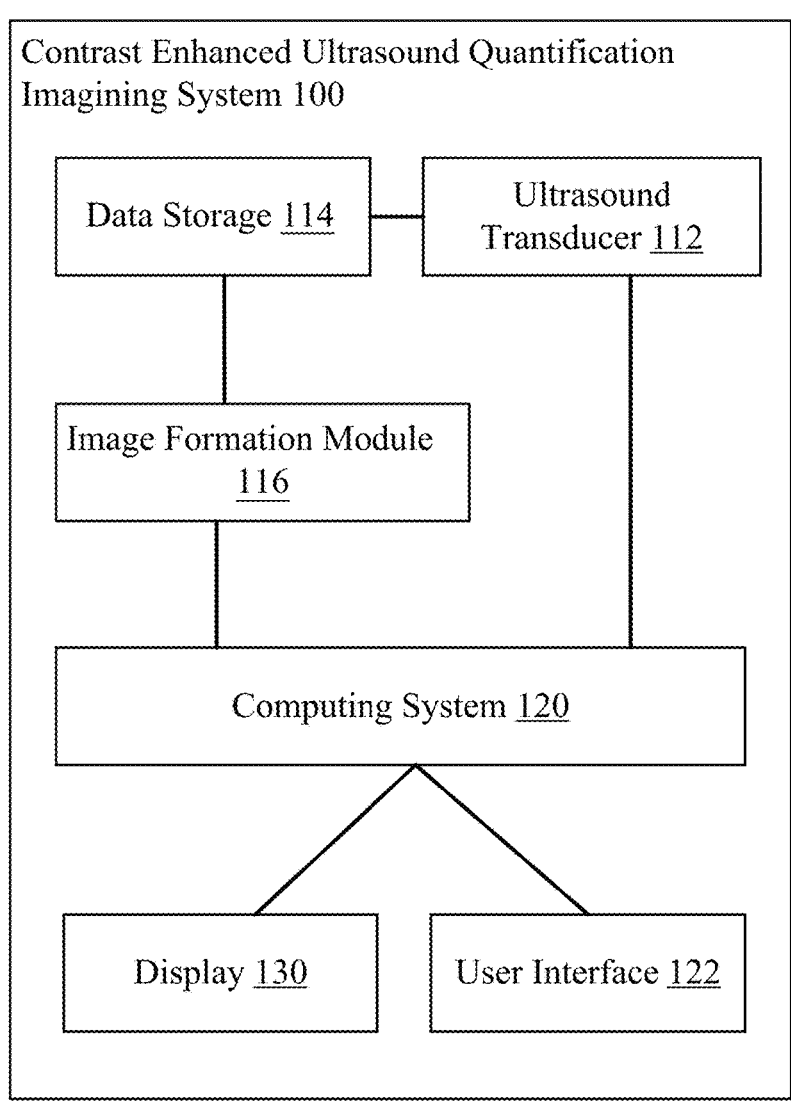
FIG. 1

Computing System 120

Obtaining Module 202

Setting Module 204

Determination Module 206

Generating Module 208

300

Threshold Gray level = 80 color bar corresponding to time

Smoothing Window Size = 15

Threshold Gray level = 80 color bar corresponding to time

Smoothing Window Size = 5

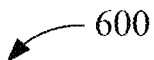

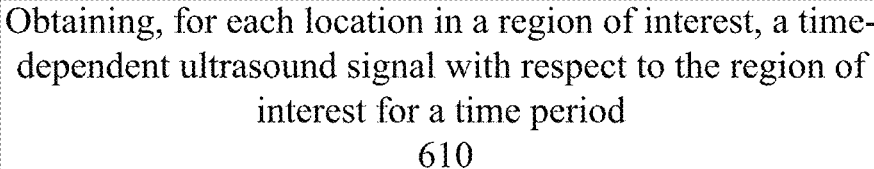

Obtaining, for each location in a region of interest, a time-dependent ultrasound signal with respect to the region of interest for a time period
610

Setting, for the each location, a global threshold for the obtained time-dependent ultrasound signal
620

Determining, for the each location, a relative time instant that the time-dependent ultrasound signal reaches the global threshold
630

Generating a structural image of the region of interest based at least on the determined relative time instant of the each location, wherein the generated structural image displays different time instants that ultrasound signals corresponding to different locations in the region of interest reach the global threshold
640

FIG. 6

SYSTEM AND METHOD FOR CONTRAST ENHANCED ULTRASOUND QUANTIFICATION IMAGING

TECHNICAL FIELD

The disclosure relates generally to contrast enhanced ultrasound quantification imaging, and in particular to methods and systems for visualization of color-coded vascular structure time sequence of contrast enhanced ultrasound quantification images.

BACKGROUND

Ultrasound imaging provides rich medical information that finds applications in diagnosis, health monitoring and assessment, etc. Many ultrasound imaging systems utilize injectable ultrasound contrast agents to achieve high-contrast images, which are desirable for visualizing organic structures inside bodies. For example, images of vascular structures may help medical experts to assess disease status and prescribe therapeutic regimens.

Traditional ultrasound imaging derives intensity information from B-mode images, which display the acoustic impedance of two-dimensional cross-sections of tissues. However, B-mode image information is insufficient for resolving weak tissue boundaries, or small vessels in the body. That is, in the B-mode image, the small vessels may appear blurry or may not be imaged at all, because of the limited resolution and the constraints of grey-scale imaging. Moreover, after the contrast agent is injected through vascular, it takes time for the concentration of agent to appreciate at a region of interest prepared for ultrasound imaging. As a result, although the ultrasound image may be enhanced over time, the image enhancement does not reflect the perfusion or flow rates of the contrast agent (or blood) in blood vessels. The medical experts are deprived of this critical information for diagnosis. Thus, there is a need to non-invasively and accurately image miniature features such as boundaries of blood vessels and provide important parameters such as perfusion of vascular structures.

SUMMARY

Various embodiments of the specification include, but are not limited to, systems, methods, and non-transitory computer readable media for contrast enhanced ultrasound quantification imaging.

In some embodiments, a non-transitory computer-readable storage medium for contrast enhanced ultrasound quantification imaging is configured with instructions executable by one or more processors to cause the one or more processors to perform operations comprising: obtaining, for each location in a region of interest, a time-dependent ultrasound signal with respect to the region of interest for a time period; setting, for the each location, a global threshold for the obtained time-dependent ultrasound signal; determining, for the each location, a relative time instant that the time-dependent ultrasound signal reaches the global threshold; and generating a structural image of the region of interest based at least on the determined relative time instant of the each location, wherein the generated structural image displays different time instants that ultrasound signals corresponding to different locations in the region of interest reach the global threshold.

In some embodiments, before the setting the global threshold, the operations further comprise: determining, for the each location, a time intensity curve based at least on the obtained time-dependent ultrasound signal for the time period.

In some embodiments, the setting, for the each location, the global threshold for the obtained time-dependent ultrasound signal comprises: determining, for the each location, a peak value of the time intensity curve; obtaining a percentage threshold; and determining, for the each location, the global threshold based at least on the peak value and the percentage threshold.

In some embodiments, the region of interest comprises a plurality of blood vessels of different sizes; and the different time instants indicate different blood perfusion rates in the plurality of blood vessels.

In some embodiments, the displayed different time instants correspond to the different locations in the region of interest and are color-coded; and the color-coded time instants displayed on the generated structural image indicate boundaries of the plurality of blood vessels.

In some embodiments, the operations further comprise: obtaining, for the each location, an updated global threshold; and updating the generated structural image based at least on the updated global threshold of the each location.

In some embodiments, before the generating the structural image, the operations further comprise: determining, based on a predetermined relative time instant and the determined relative time instant of the each location, one or more locations showing abnormality; and the generated structural image comprises one or more labels indicating the one or more locations showing abnormality.

In some embodiments, before the generating the structural image, the operations further comprise: obtaining a window size for image smoothing; and the generating the structural image of the region of interest based at least on the determined relative time instant of the each location comprises: generating the structural image of the region of interest based at least on the window size and the determined relative time instant of the each location.

In some embodiments, before the obtaining the time-dependent ultrasound signal, the operations further comprise: obtaining a user-input to determine an end of the time period.

In some embodiments, a system for contrast enhanced ultrasound quantification imaging comprises one or more processors and one or more non-transitory computer-readable memories coupled to the one or more processors and configured with instructions executable by the one or more processors to cause the one or more processors to perform operations comprising: obtaining, for each location in a region of interest, a time-dependent ultrasound signal with respect to the region of interest for a time period; setting, for the each location, a global threshold for the obtained time-dependent ultrasound signal; determining, for the each location, a relative time instant that the time-dependent ultrasound signal reaches the global threshold; and generating a structural image of the region of interest based at least on the determined relative time instant of the each location, wherein the generated structural image displays different time instants that ultrasound signals corresponding to different locations in the region of interest reach the global threshold.

In some embodiments, a method for contrast enhanced ultrasound quantification imaging comprises: obtaining, for each location in a region of interest, a time-dependent ultrasound signal with respect to the region of interest for a time period; setting, for the each location, a global threshold for the obtained time-dependent ultrasound signal; determining, for the each location, a relative time instant that the time-dependent ultrasound signal reaches the global threshold; and generating a structural image of the region of interest based at least on the determined relative time instant of the each location, wherein the generated structural image displays different time instants that ultrasound signals corresponding to different locations in the region of interest reach the global threshold.

In some embodiments, a system for contrast enhanced ultrasound quantification imaging comprises: an ultrasound transducer configured to emit and receive ultrasound waves reflected from a region of interest and generate ultrasound signals based on the received ultrasound waves; and a computing system comprising: one or more processors, and one or more non-transitory computer-readable storage media coupled to the one or more processors and having instructions stored thereon that are executable by the one or more processors to cause the one or more processors to perform operations. The operations comprise: obtaining, for each location in the region of interest, a time-dependent ultrasound signal with respect to the region of interest for a time period from the generated ultrasound signals; setting, for the each location, a global threshold for the obtained time-dependent ultrasound signal; determining, for the each location, a relative time instant that the time-dependent ultrasound signal reaches the global threshold; and generating a structural image of the region of interest based at least on the determined relative time instant of the each location, wherein the generated structural image displays different time instants that ultrasound signals corresponding to different locations in the region of interest reach the global threshold.

Embodiments disclosed herein have one or more technical effects. In some embodiments, the methods and systems may provide visualization of tissue, vascular, or other structures in a region of interest with great accuracy. For example, the visualization may be implemented through color-coding different parts (e.g., locations down to pixel level) of the region of interest based on different time instants. The time instants may be determined based on ultrasound signals corresponding to different parts reach a global threshold. In one embodiment, with the disclosed contrast enhanced ultrasound quantification imaging methods, miniature features such as boundaries of blood vessels may be resolved. In other embodiments, the generated images provides visualization of boundaries of vascular structures, such as blood vessels of different sizes based on coded colors. This allows an user to observe miniature sizes features (e.g. capillaries) directly on the ultrasound images. In still other embodiments, the generated images provide information of perfusion rates in vascular structures. In some embodiments, the vascular structures and the perfusion rates provide critical information that allows users to recognize abnormal areas based on the coded colors. In one embodiment, a computer may compare the generated image with a baseline (e.g., flow rate data or tissue image for a health body), and based on the comparison, pinpoint on the generated image locations (e.g., at the issue level) causing health issues.

These and other features of the systems, methods, and non-transitory computer readable media disclosed herein, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention. It is to be understood that the foregoing general description and the following detailed description are exemplary and explanatory only, and are not restrictive of the invention, as claimed.

BRIEF DESCRIPTION OF THE DRAWINGS

FIG. 1 illustrates an exemplary environment of contrast enhanced ultrasound quantification imaging system, in accordance with various embodiments.

FIG. 6 depicts a flowchart of an exemplary method for contrast enhanced ultrasound quantification imaging, in accordance with various embodiments.

DETAILED DESCRIPTION

Figure 2:
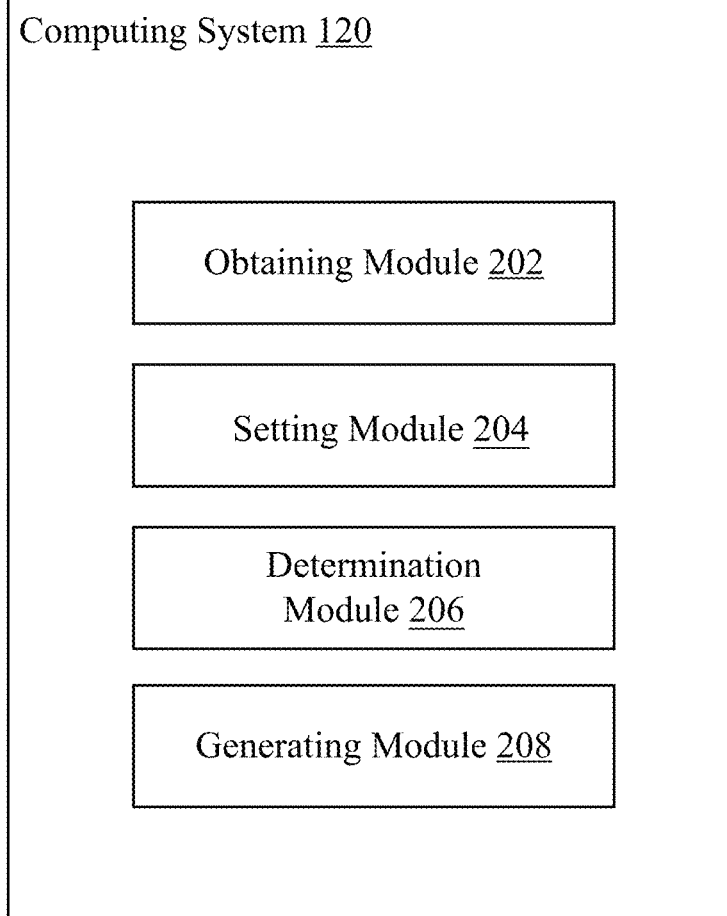
FIG. 2 illustrates an exemplary computing system for contrast enhanced ultrasound quantification imaging, in accordance with various embodiments.

FIG. 1 illustrates an exemplary environment of contrast enhanced ultrasound quantification imaging (CEUS QI) system 100 for contrast enhanced ultrasound quantification imaging, in accordance with various embodiments. Depending on the implementation, the CEUS QI system 100 may include additional, fewer, or alternative components.

In some embodiments, the CEUS QI system 100 may include an ultrasound transducer 112, a data storage 114, an image formation module 116, a computing system 120, a user interface 122, and a display 130, one or more of which may be optional. The ultrasound transducer 112 may couple to the data storage 114 and the computing system 120, the data storage 114 may couple to the image formation module 116, the image formation module 116 may couple to the computing system 120, and the computing system 120 may couple to the display 130 and the user interface 122. Any coupled modules may transmit signals between each other. The ultrasound transducer 112, the data storage 114, the image formation module 116, the computing system 120, the user interface 122, and the display 130 may be integrated in a single system or device or be distributed in several connected systems or devices.

In some embodiments, an object 102 (e.g., a human, a pet, a tissue section, a live sample) may be prepared for CEUS QI with respect to a region of interest (ROI), such as belly, heart, etc. For example, a human may be injected with a contrast agent through vascular injection, after which the ROI may be exposed to ultrasound waves. In one embodiment, the computing system 120 may trigger the ultrasound transducer 112 to emit ultrasound waves towards the ROI. For example, the ultrasound transducer may be placed on a patient's body, allowing ultrasound waves to emit towards the ROI on the body. The ROI may contain skin, nail, hair, or the like of a body surface, under which various organic structures (e.g., tissue, blood vessel) may reflect back the ultrasound waves in various degrees. In one embodiment, there may be a plurality of different blood vessels such as arteries, veins, and capillaries of various sizes in the ROI. In some embodiments, the ultrasound transducer 112 may include a detector. The detector may be configured to receive ultrasound waves reflected from the ROI and generate ultrasound signals based on the received ultrasound waves. For example, the detector may convert the reflected ultrasound waves into the electrical signals to obtain ultrasound signals. In some embodiments, the ultrasound transducer 112 may send the ultrasound signals to the data storage 114. The data storage 114 may be configured to store the ultrasound signals generated from the ultrasound transducer 112 and send to the image formation module 116. The image formation module 116 may be optional and configured to adjust the ultrasound signal amplitudes and phases, for example, by performing a delay for focus, weighting, channel summation, etc. Then, the image formation module 116 may send the adjusted ultrasound signals to the computing system 120 to undergo related signal processes. The computing system 120 may be a system for CEUS QI. The signal process for the CEUS QI is described below with respect to FIG. 2.

In some embodiments, depending on different imaging modes requested through the user interface 122, the computing system 120 may perform different processes on the ultrasound signals to generate corresponding images. For example, the intensity of the ultrasound signals and intensity variations for each location in the ROI may be recorded for the time period to generate the images. The quantification images may be displayed on the display 130 to the user. Through the user interface 122, the user may update request configurations or otherwise input instructions to modify the images, for example, changing display modes.

FIG. 2 illustrates an exemplary computing system 120 for CEUS QI, in accordance with various embodiments. Depending on the implementation, the computing system 120 may include additional, fewer, or alternative components.

In some embodiments, the computing system 120 for CEUS QI may include one or more processors (e.g., a digital processor, an analog processor, a digital circuit designed to process information, a central processing unit, a graphics processing unit, a microcontroller or microprocessor, an analog circuit designed to process information, a state machine, and/or other mechanisms for electronically processing information) and one or more non-transitory computer-readable memories (e.g., permanent memory, temporary memory, non-transitory computer-readable storage medium) coupled to each other. The one or more memories may be configured with instructions executable by the one or more processors. The processor(s) may be configured to perform various operations by interpreting machine-readable instructions stored in the memories. The computing system 120 may include other computing resources. The computing system 120 may be installed with appropriate software (e.g., ultrasound imaging control program) and/or hardware (e.g., wires, wireless connections) to access other computing resources.

In some embodiments, the computing system 120 for CEUS QI may include an obtaining module 202, a setting module 204, a determination module 206, and a generating module 208. That is, the obtaining module 202, the setting module 204, the determination module 206, and the generating module 208 may be implemented as software (e.g., a part of software instructions), as hardware, or as a combination of software and hardware. As software instructions, the various modules may be executed by the one or more processors of the computing system 120 to perform various operations.

While the computing system 120 for CEUS QI is shown in FIG. 2 as a single entity, this is merely for ease of reference and is not meant to be limiting. One or more of the modules or one or more functionalities of the computing system 120 described herein may be implemented in a single computing device or distributed in multiple computing devices. In some embodiments, one or more of the modules or one or more functionalities of the computing system 120 described herein may be implemented in one or more networks (e.g., an enterprise network accessible to an ultrasound machine), one or more endpoints (e.g., in an ultrasound machine), one or more servers (e.g., a server connected to an ultrasound machine), one or more clouds (e.g., a could accessible to an ultrasound machine), etc.

In some embodiments, the obtaining module 202 may be configured to obtain, for each location of an ROI, a time-dependent ultrasound signal with respect to the ROI for a time period from CEUS images. The CEUS images for the time period may be generated based on intensity variations for the each location of the ROI, and stored in the computing system 120 for CEUS QI. Collectively for the entire ROI, the obtained information from the CEUS images may include ultrasound signals received for the time period. Obtaining information may include one or more of accessing, acquiring, analyzing, determining, examining, identifying, loading, locating, opening, receiving, retrieving, reviewing, storing, or otherwise obtaining the information. The ultrasound signal may be transmitted from the ultrasound transducer 112 or the image formation module 116 as described above, or otherwise obtained by the computing system 120. For the time-dependent ultrasound signal, the ultrasound signal may be obtained for the time period to capture time-dependent variations in intensity or one or more other parameters. The ROI may refer to a two-dimensional surface of any size (e.g., a body surface, a cross-section under a body surface), and the obtained ultrasound signal may be derived at least from ultrasound waves reflected by structures (e.g., blood vessels of different sizes, tissues between the blood vessels) at any depth below the surface. Alternatively, the ROI may refer to a three-dimensional space of any size (e.g., a volume under a body surface).

The CEUS QI may be performed while the contrast agent is injected and passes through the ROT. The CEUS images may be generated in real time based on the contrast enhanced ultrasound signals of each location of the ROT. For example, the intensity of the ultrasound signals and intensity variations for each location in the ROI may be recorded in real time to generate the CEUS images. In other words, the time-dependent ultrasound signal is generated and received in response to the injection of contrast agent to the patient and the corresponding CEUS images are generated and stored as the input to the CEUS QI system.

In some embodiments, before or after obtaining the time-dependent ultrasound signal, the computing system 120 (e.g., another obtaining module) may be configured to obtain a user-input to determine an end of the time period. For example, the computing system 120 may obtain, through the user interface 122, an end frame. The end frame may refer to an end of the time period of the CEUS QI. For another example, the computing system 120 may be configured to set the end frame. With the end frame, the computing system 120 may obtain ultrasound signals for the locations in the ROI from or after a time of injection of the contrast agent until the end frame to improve efficiency and optimize storage. Similarly, the computing system 120 (e.g., another obtaining module) may be configured to obtain a user-input to determine a start of the time period (e.g., a start frame). The obtained ultrasound signals may be transmitted to the setting module 204 for further processing.

In some embodiments, before or after obtaining the time-dependent ultrasound signal, the computing system 120 (e.g., another obtaining module) may be configured to obtain a percentage threshold. The percentage threshold may be a parameter (e.g., 50%) used for CEUS QI described below. For example, the computing system 120 may obtain the percentage threshold through the user interface 122. For another example, the computing system 120 may be configured to set the percentage threshold. The obtained percentage threshold may be transmitted to the setting module 204 for further processing. The percentage threshold may be adjustable in real time, which may cause the generated images to update in real time.

In some embodiments, the setting module 204 may be configured to set, for the each location, a global threshold for the obtained time-dependent ultrasound signal. The global threshold may be a threshold signal that the same threshold signal is applied to the each location of the ROI. The global threshold may refer to a predetermined threshold for the obtained signal. The global threshold may be determined through one or more steps. In one embodiment, the setting module 204 may be configured to determine, for the each location, a Time Intensity Curve (TIC) based at least on the obtained time-dependent ultrasound signal for the time period. For example, the setting module 204 may organize the obtained time-dependent ultrasound signal of the location into the TIC. The TIC may depict the intensity variation of the ultrasound signal for the period of time. Then, the setting module 204 may set the global threshold for the location in the ROI based on the corresponding TIC and the obtained percentage threshold. The TIC for is described in more details with reference to FIG. 3A, the same process may be repeated for all locations in the ROI.

Figure 3A:
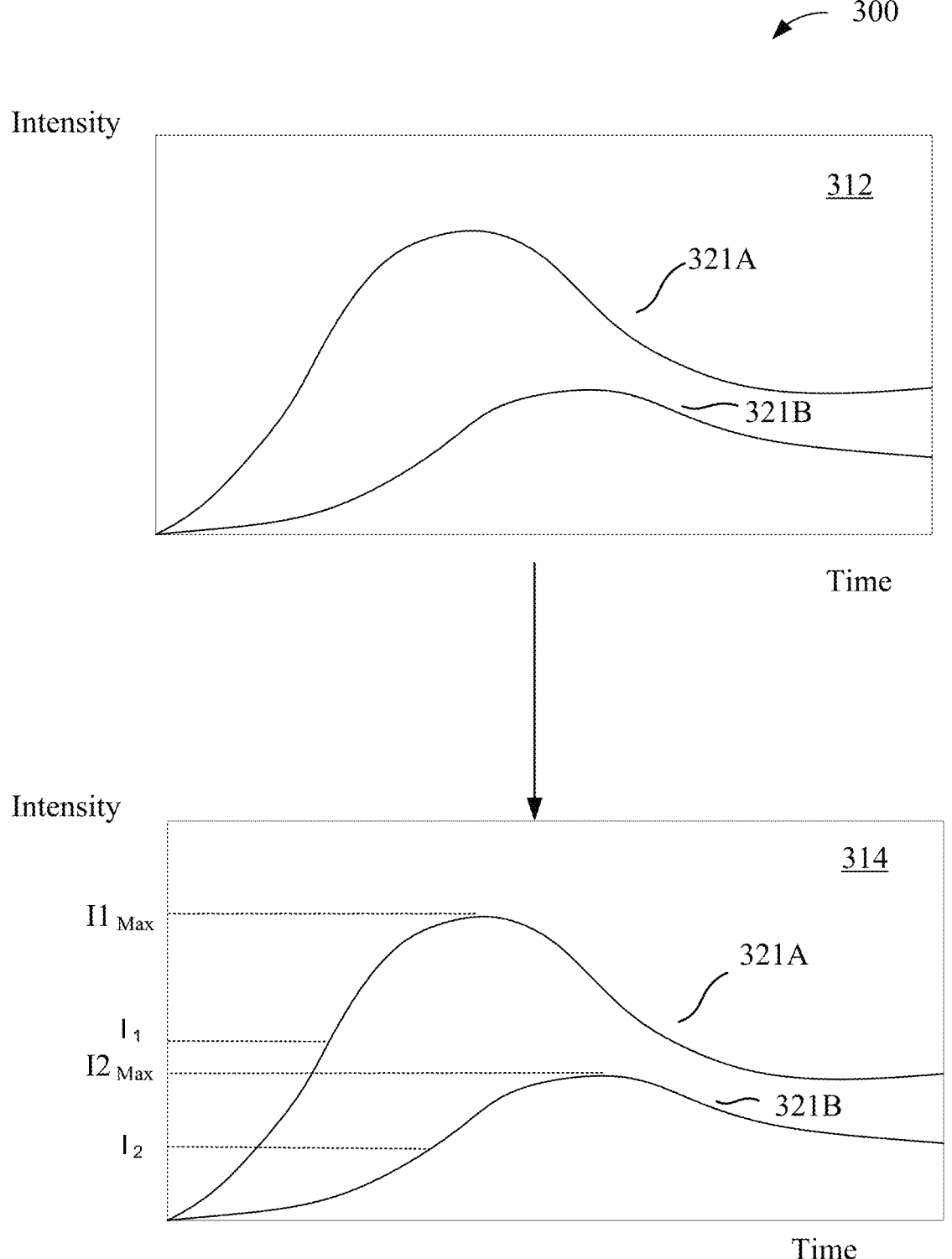
FIGS. 3A-3B illustrate exemplary work flows of a setting module, in accordance with various embodiments.

Referring to FIG. 3A, FIG. 3A illustrates an exemplary work flow 300 of the setting module 204, in accordance with various embodiments. In some embodiments, the setting module 204 may determine, for the each location, a peak value of the time intensity curve; obtain the percentage threshold; and determine, for the each location, the global threshold based at least on the peak value and the percentage threshold. As shown in FIG. 3A, based on the obtained time-dependent ultrasound signal for locations A and B, the setting module 204 may determine the intensity variations of the corresponding ultrasound signals for the time period. The locations A and B may correspond to different spots on different structures within the ROI. As shown in diagram 312, the intensity variation for location A is represented by TIC 321A, and the intensity variation for location B is represented by TIC 321B. As shown, the TICs are plotted against an x-axis of frame time and an y-axis of signal intensity. The data points in the TICs may be fitted with smooth functions. In one example, location A and TIC 321A may correspond to a wider blood vessel (e.g., artery), and location B and TIC 321B may correspond to a finer blood vessel (e.g., capillary).

In some embodiments, to set the global threshold for each location, the setting module 204 may first determine a peak value (i.e., $I_{max}$). The peak value at each location may be determined based on the obtained time-dependent ultrasound signal. For ease of illustration, the peak value at locations A and B as shown are determined based on the TICs 321A and 321B. For example, as shown in diagram 314, the peak value at the location A may be determined to be the maximum intensity $I1_{max}$ of the curve 321A, and the peak value at the location B may be determined to be the maximum intensity $I2_{max}$ of the curve 321B. Since the contrast agent reaches different spots at different times, the contrast enhancement in different locations may vary, and the $I_{max}$ for each location may be different.

In some embodiments, with $I_{max}$, the setting module 204 may be configured to set the global threshold based on the $I_{max}$ and the obtained percentage threshold. For example, when the obtained percentage threshold is 50%, the setting module 204 may be configured to determine the global threshold for the each location in the ROI as $I_{max}*50\%$. For example, the global thresholds at the locations A and B may be determined to be $I_1$ and $I_2$ respectively, based on the determined peak values $I1_{max}$ and $I2_{max}$ and the percentage threshold 50%. For example, as shown in the diagram 314, the global threshold $I_1$ for location A may be determined to be $I1_{max}$ times 50%, and the global threshold $I_2$ for location B may be determined to be $I2_{max}$ times 50%.

Referring back to FIG. 2, in some embodiments, the determination module 206 may be configured to determine, for the each location, a relative time instant that the time-dependent ultrasound signal reaches the global threshold. The relative time instant means that the time instant may not need to be an absolute measurement of time, as long as showing relativeness with among different time instants. The relativeness may be a basis for color coding described later. In one embodiment, the relative time instant for a location in the ROI may be determined and recorded when the ultrasound signal for the location reaches its corresponding global threshold for the first time. The process is described in more details with reference to FIG. 3B.

Figure 3B:
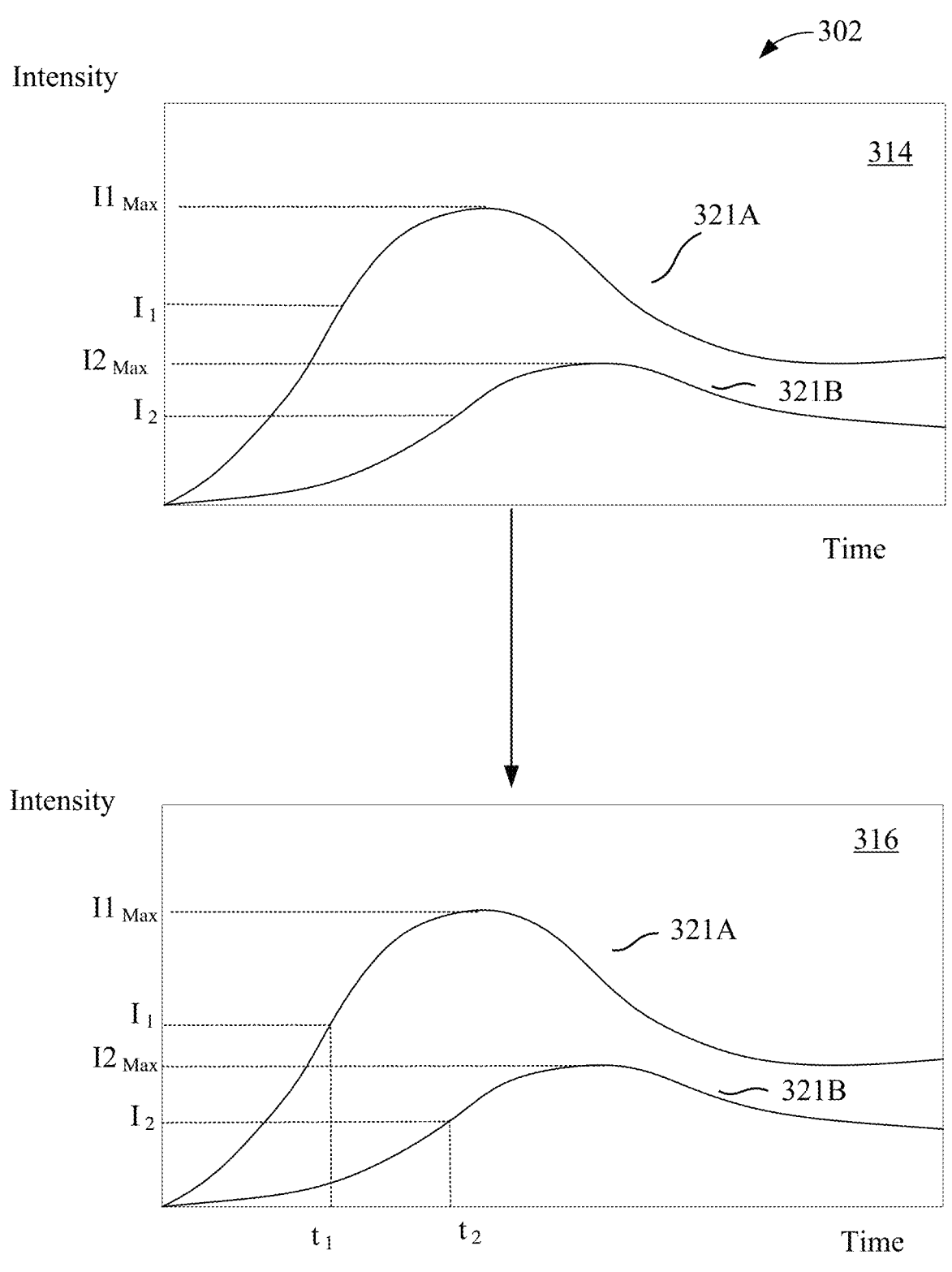

Referring to FIG. 3B, FIG. 3B illustrates an exemplary work flow 302 of the determination module 206, in accordance with various embodiments. As shown in FIG. 3B, the diagram 314 is the same as described above. Then, as shown in diagram 316, the determination module 206 may be configured to determine time instants corresponding to the determined global thresholds $I_1$ and $I_2$. In some embodiments, the determined time instant may be the first time moment when the ultrasound signal for each location reaches the corresponding global threshold. For example, the determination module 206 may determine based on curve 321A a time moment $t_1$ as the relative time instant that the ultrasound signal at the location A reaches the global threshold $I_1$ for the first time, and determine a time moment $t_2$ as the relative time instant that the ultrasound signal at the location B reaches the global threshold $I_2$ for the first time. The same process may be implemented on each location in the ROI to determine the corresponding relative time instant.

Referring back to FIG. 2, in some embodiments, the generating module 208 may be configured to generate a structural image of the ROI based at least on the determined relative time instant of each location. The structural image may refer to an image of organic structures (e.g., tissue structure, blood vessel structure) for the ROT. The generated structural image may display different time instants that ultrasound signals corresponding to different locations in the region of interest reach the global threshold, for example, through color coding. In one embodiment, the generating module 208 may be configured to code the different relative time instants with different colors to generate the structural image. The coded colors may include grey scale colors, RGB colors, etc. The different time instants may correspond to different colors in the corresponding spectrum. For example, when the determined relative time instant of a first location is the same as the determined relative time instant of a second location in the ROI, the first and second location may be coded with the same color. In another example, when the determined relative time instant of the first location is different from the determined relative time instant of a third location in the ROI, the color coded at the first location may be different from the color coded at the third location. The generated images are illustrated in FIGS. 4A and 4B.

Figure 4A:
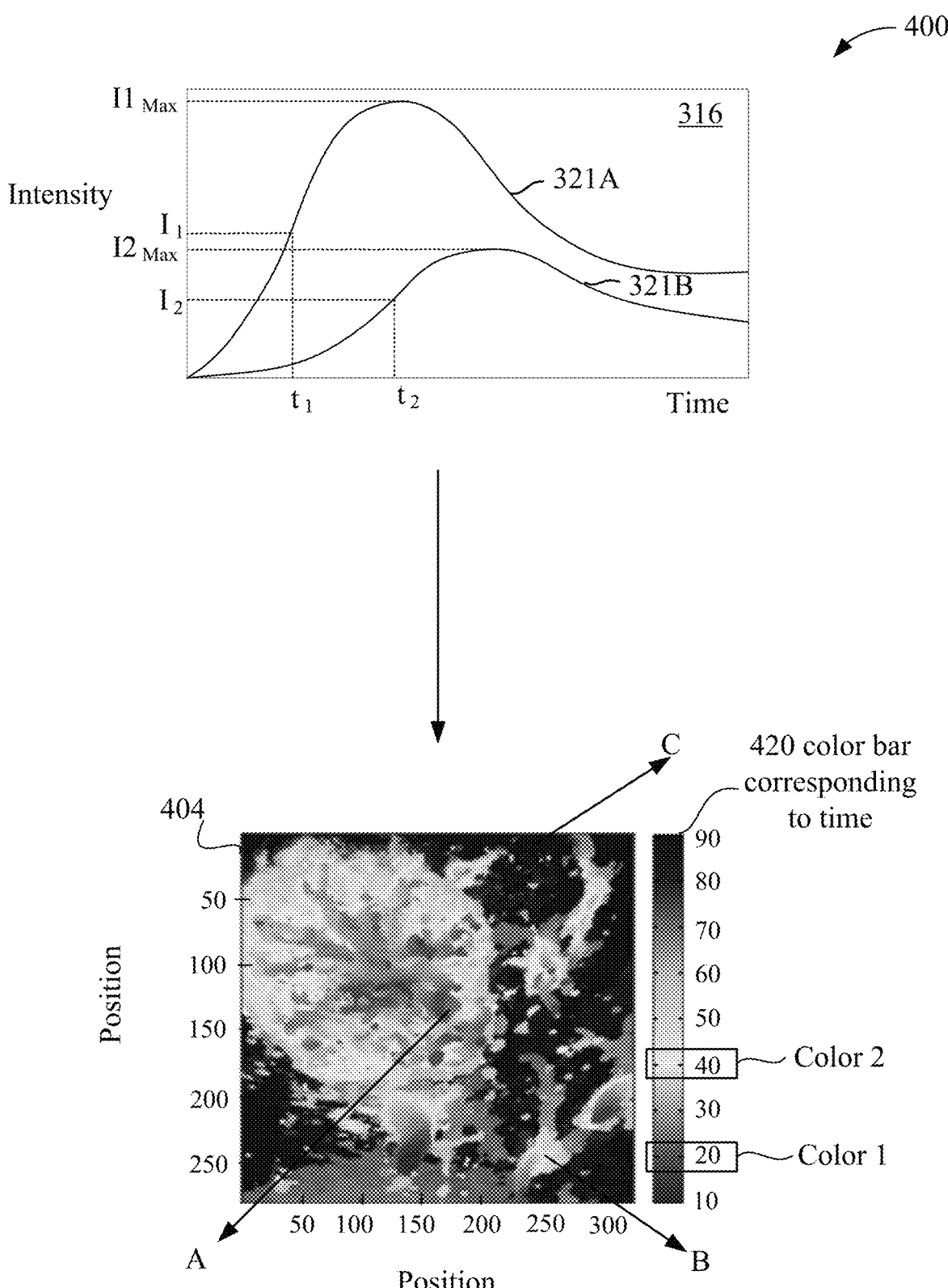
FIGS. 4A-4B illustrate exemplary work flows of a determination module and a generating module, in accordance with various embodiments.
Figure 4B:
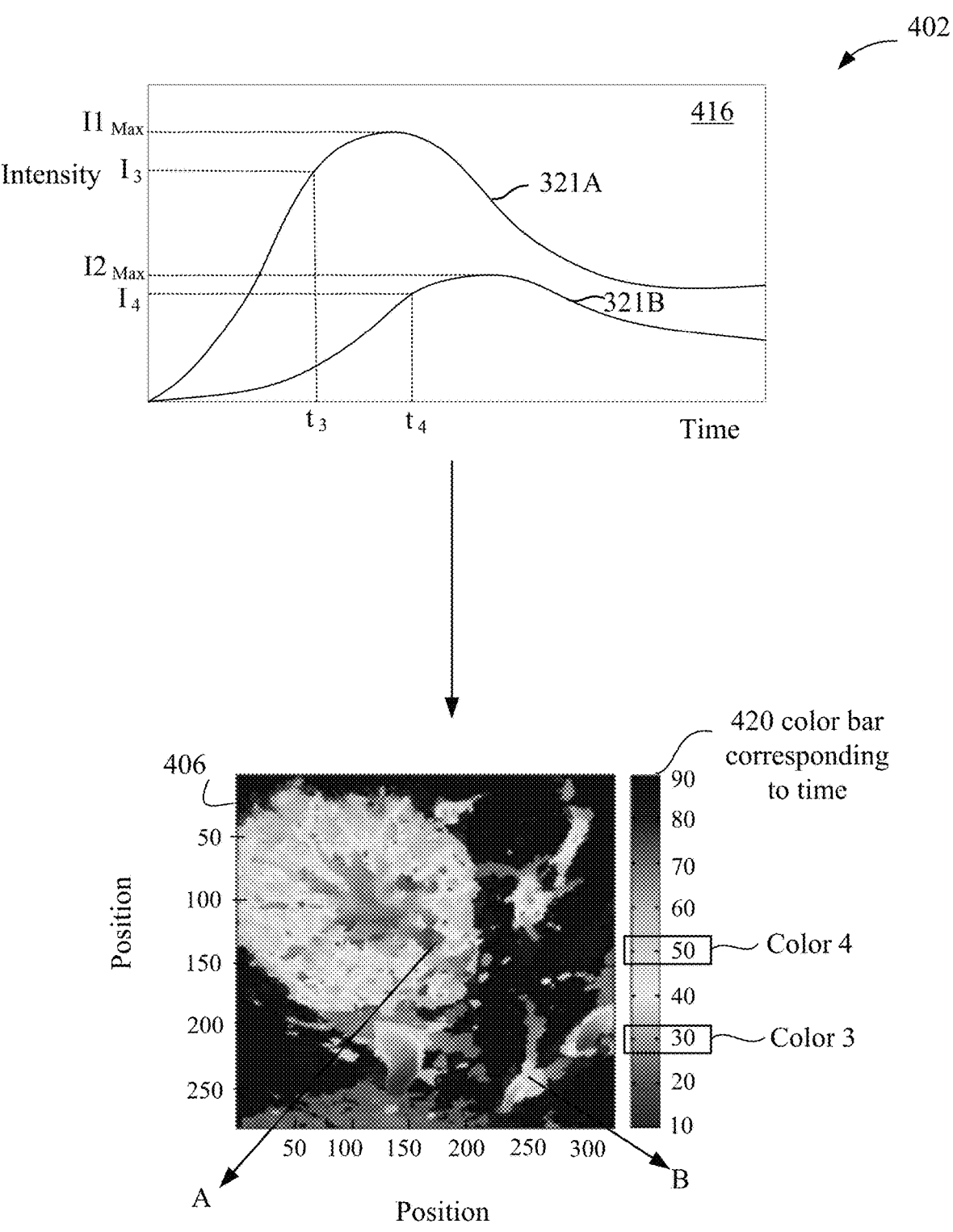

FIG. 4A illustrates an exemplary work flow 400 of the generating module 208, in accordance with various embodiments. As shown in FIG. 4A, the diagram 316 is the same as described above. In some embodiments, the generating module 208 may generate a structural image 404 with color codes (e.g., from a color palette 420) for various locations in the ROI based on their relative time instants. The color palette 420 may refer to color codes that correspond to relative time instants. The image 404 may show the ROI in two dimensions (e.g., x-y coordinates) for indicating relative positions. For example, one or more pixels of the image 404 may correspond to a location in the ROT. The location may be color-coded based on its corresponding relative time instant. For example, as in the diagram 316, the determination module 206 may determine that the relative time instant $t_1$ for the location A is 20, and the relative time instant $t_2$ for the location B is 40. The location A may be on an artery, and the location B may be on a capillary. Accordingly, based on the color palette 420, the generating module 208 may code the location A with color 1 and code the location B with color 2 to reflect the different time instants. After all locations in the ROI are color-coded, the image 404 may be generated in colors providing a visualization of the ROI.

The generated image may provide rich medical information. In some embodiments, the displayed different time instants may correspond to the different locations in the ROI and are color-coded, and the color-coded time instants displayed on the generated structural image may indicate boundaries of the plurality of blood vessels. In one embodiment, the generated image displays various regions in different colors, and the color region boundaries may indicate boundaries of different organic structures, such as blood vessels that receive the injected contrast agent at different rates. For example, the location A coded with color 1 and the location B coded with color 2 may indicate that the two locations correspond to different biological parts, such as two locally different blood vessels. As shown in FIG. 4A, the color region around location A indicates a faster reception of the contrast agent to reach its global threshold and renders a cross-sectional shape of an artery in the ROI, while the color region around location B indicates a later reception of the contrast agent to reach its global threshold and renders a cross-sectional shape of a capillary in the ROI. The vast background of the image (e.g., location C) may indicate tissue regions that are the slowest to receive the contrast agent. Thus, different organic structures inside the body may be imaged in colors and visualized. Based on the generated image, the computing system 120 may measure the sizes of the blood vessels.

Further, the time-based color-coding may distinguish finer features at a high resolution level. For example, locations on the same cross section of the artery around location A may be coded in various shades of colors based on their relative time instants, which may be affected by the distance and location from the center of the cross-section. Since the artery inner wall may have unsmooth structures that cause uneven agent-carrying blood flow rate, features of such inner walls may be resolved by the color coding. As shown in the image 404, the fine structures of the inner walls are resolved at least because the unevenness slows down the blood flow at locations closer to the wall which causes increasing relative time instants.

In some embodiments, the generated structural image may provide blood profusion rate information. For example, the ROI may comprise a plurality of blood vessels of different sizes, and the different time instants indicate different blood perfusion rates in the plurality of blood vessels. The perfusion rates of the contrast agent as carried by blood in different blood vessels may be affected by of the vessel size, distance from the injection spot, etc. Since the generated structural image displays different relative time instants for the locations in different colors, the different colors may indicate different blood perfusion rates in different blood vessels. If the relative time instant of a first location is larger than that of a second location, the perfusion rate at the first location may be slower than that at the second location. For example, since the relative time instant of the location B is larger than that of the location A, the perfusion rate at the location B may be slower than that at the location A. That is, according to the generated image, the artery around location A appears to receive the contrast agent faster than the capillary around location B.

In some embodiments, the computing system 120 for CEUS QI may be configured to determine one or more locations showing abnormality. In one embodiment, before the generating the structural image, the computing system 120 may determine, based on a predetermined relative time instant (e.g., a baseline) and the determined relative time instant of the each location, one or more locations showing abnormality, and the generated structural image may comprise one or more labels indicating the one or more locations showing abnormality. For example, the computing system 120 may compare the relative time instants with the baseline (e.g., flow rate data for a healthy body). Alternatively, the computing system 120 may compare the generated image with a baseline image for a healthy body for the comparison. For example, a predetermined relative time instant of a first location in a ROI from a healthy person may be coded with color 1. If the determined relative time instant of the same first location in the same ROI from a patient is coded with color 2 in the structural image, the computing system 120 may determine abnormality at the first location. Based on either type of comparison, the computing system 120 may pinpoint on the generated image one or more locations (e.g., at the issue level) potentially causing health issues. The generating module 208 may then be configured to indicate the one or more locations showing abnormality on the generated image, by example, by labelling, highlighting, etc. The pinpointed location may be an indication of source for cancer cell, malignant tissue, vessel clog, etc.

FIG. 4B illustrates another exemplary work flow 402 of the generating module 208, in accordance with various embodiments. In some embodiments, the global thresholds for the locations in the ROI may be changed based on an update of the percentage threshold, and the computing system 120 may adjust the generated structural image accordingly in real time. In one embodiment, the computing system 120 may be configured to obtain, for the each location, an updated global threshold. The generating module 208 may be configured to update the generated structural image based at least on the updated global threshold of the each location. For example, in the diagram 316 in FIG. 4A, the threshold percentage is 50% before the update. By the update, the threshold percentage becomes 80%. As shown in the diagram 416 in FIG. 4B, for location A, at the time moment $t_3$ (e.g., relative time instant 30), the global threshold $I_3$ reaches 80% of the peak intensity of the curve 321A for the first time. Accordingly, location A is re-coded with color 3 in an image 406. As another example, for location B, at the time moment $t_4$ (e.g., relative time instant 50), the global threshold $I_4$ reaches 80% of the peak intensity of the curve 321B for the first time. Accordingly, the location B is re-coded with color 4 in the image 406. The same update may be performed for all locations in the ROI and all pixels in the generated image. Correspondingly, as shown in the structural image 406 in FIG. 4B, the structural image is re-coded based on the updates to the relative time instants.

Figures 5A, 5B:
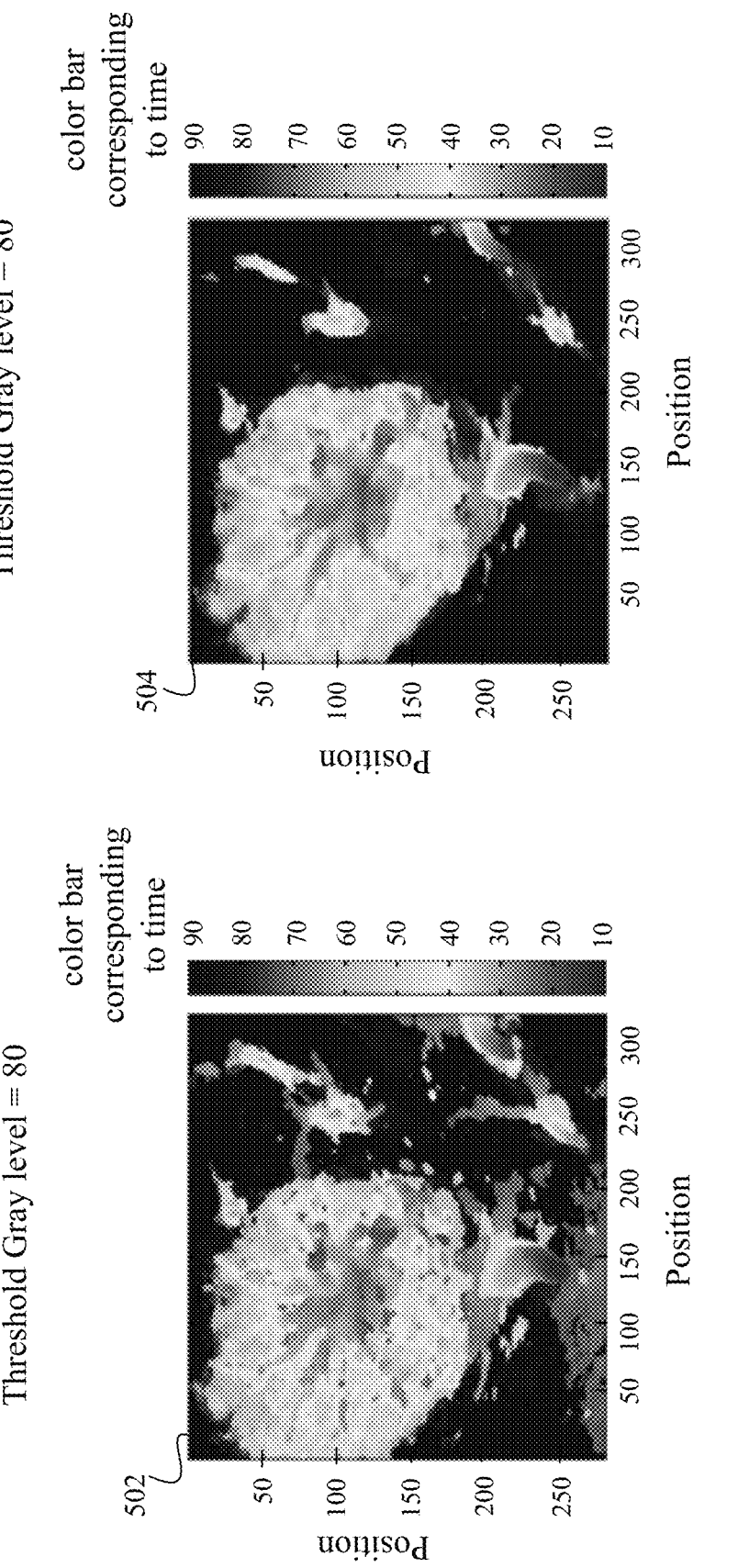
FIGS. 5A-5B illustrate examples of generated structural images, in accordance with various embodiments.

FIGS. 5A and 5B illustrate examples of generated structural images 502, 504, in accordance with various embodiments. The two structural images 502 and 504 are shown with different smoothing window sizes at the same percentage threshold (e.g., threshold Gray level=80). The smoothing window may be implemented by a smoothing function in image processing. Applying the smoothing window may reduce signal noise of individual pixels that higher than signals of adjacent pixels to create a smoother image. In some embodiments, the image 504 may be generated with the input smoothing window size 15, and the image 502 may be generated with the input smooth window size 5. Like the percentage threshold, the smoothing window size may be determined and adjusted through the user interface 122 or set by the computing system 120.

In some embodiments, before the generating the structural image, the computing system 120 may obtain a window size for image smoothing, and the generating module 208 may generate the structural image of the region of interest based at least on the window size and the determined relative time instant of the each location. By adjusting the smoothing window size, the computing system 120 may reduce signal noise of the generated images, with a trade-off for losing resolution of smaller features. For example, as shown in FIG. 5A when the input of the smoothing window size is 5, the generated structural image 502 may resolve various fine vascular structures. When the input of the smoothing window size is adjusted to 15 in FIG. 5B, the generated image 504 may produce a smoother image compared to the structural image 502, but many small features blend into the background and are not resolved.

FIG. 6 illustrates a flowchart of an exemplary method 600, according to various embodiments of the present disclosure. The method 600 may be performed by one or more components of the CEUS QI system 100, such as the computing system 120 for CEUS QI. The operations of the method 600 presented below are intended to be illustrative. Depending on the implementation, the method 600 may include additional, fewer, or alternative steps performed in various orders or in parallel.

Block 610 comprises obtaining, for each location in a region of interest, a time-dependent ultrasound signal with respect to the region of interest for a time period. Block 620 comprises setting, for the each location, a global threshold for the obtained time-dependent ultrasound signal. Block 630 comprises determining, for the each location, a relative time instant that the time-dependent ultrasound signal reaches the global threshold. Block 640 comprises generating a structural image of the region of interest based at least on the determined relative time instant of the each location, wherein the generated structural image displays different time instants that ultrasound signals corresponding to different locations in the region of interest reach the global threshold.

In some embodiments, before the setting the global threshold, the method 600 further comprises: determining, for the each location, a time intensity curve based at least on the obtained time-dependent ultrasound signal for the time period.

In some embodiments, the setting, for the each location, the global threshold for the obtained time-dependent ultrasound signal comprises: determining, for the each location, a peak value of the time intensity curve; obtaining a percentage threshold; and determining, for the each location, the global threshold based at least on the peak value and the percentage threshold.

In some embodiments, the region of interest comprises a plurality of blood vessels of different sizes; and the different time instants indicate different blood perfusion rates in the plurality of blood vessels.

In some embodiments, the displayed different time instants correspond to the different locations in the region of interest and are color-coded; and the color-coded time instants displayed on the generated structural image indicate boundaries of the plurality of blood vessels.

In some embodiments, the method 600 further comprises: obtaining, for the each location, an updated global threshold; and updating the generated structural image based at least on the updated global threshold of the each location.

In some embodiments, before the generating the structural image, the method 600 further comprises: determining, based on a predetermined relative time instant and the determined relative time instant of the each location, one or more locations showing abnormality; and the generated structural image comprises one or more labels indicating the one or more locations showing abnormality.

In some embodiments, before the generating the structural image, the method 600 further comprises: obtaining a window size for image smoothing; and the generating the structural image of the region of interest based at least on the determined relative time instant of the each location comprises: generating the structural image of the region of interest based at least on the window size and the determined relative time instant of the each location.

In some embodiments, before the obtaining the time-dependent ultrasound signal, the operations further comprise: obtaining a user-input to determine an end of the time period.

Figure 7:
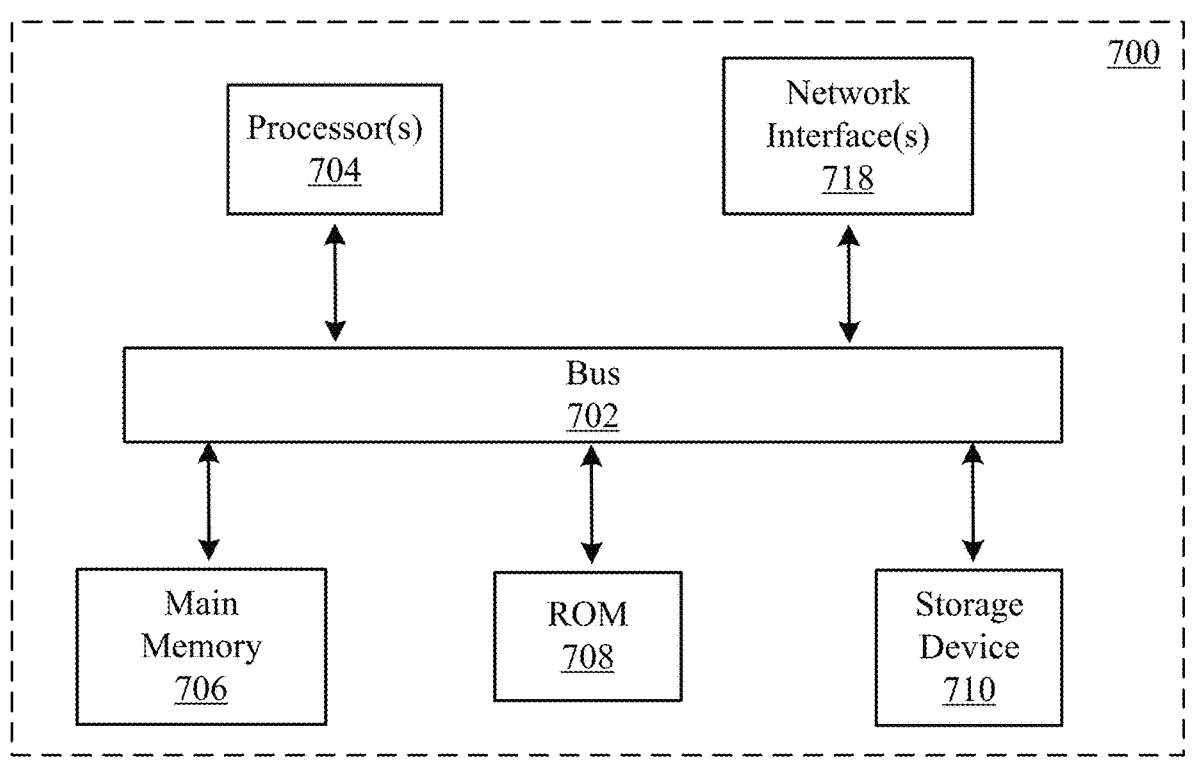
FIG. 7 is a block diagram that illustrates a computer system upon which any of the embodiments described herein may be implemented.

FIG. 7 is a block diagram that illustrates a computer system 700 upon which any of the embodiments described herein may be implemented. The computer system 700 may be implemented in any of the components of the devices, apparatuses, or systems illustrated in FIGS. 1-6. For example, the computing system 120 may implement the computer system 700. One or more of the methods described with reference to FIGS. 1-6, such as the method 600, may be performed by one or more implementations of the computer system 700. The computer system 700 includes a bus 702 or other communication mechanism for communicating information, one or more hardware processors 704 coupled with bus 702 for processing information. Hardware processor(s) 704 may be, for example, one or more general purpose microprocessors.

The computer system 700 may include a bus 702 or other communication mechanism for communicating information, one or more hardware processor(s) 704 coupled with bus 702 for processing information. Hardware processor(s) 704 may be, for example, one or more general purpose microprocessors.

The computer system 700 may also include a main memory 706, such as a random-access memory (RAM), cache and/or other dynamic storage devices, coupled to bus 702 for storing information and instructions executable by processor(s) 704. Main memory 706 also may be used for storing temporary variables or other intermediate information during execution of instructions executable by processor(s) 704. Such instructions, when stored in storage media accessible to processor(s) 704, render computer system 700 into a special-purpose machine that is customized to perform the operations specified in the instructions. The computer system 700 may further include a read only memory (ROM) 708 or other static storage device coupled to bus 702 for storing static information and instructions for processor(s) 704. A storage device 710, such as a magnetic disk, optical disk, or USB thumb drive (Flash drive), etc., may be provided and coupled to bus 702 for storing information and instructions.

The computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the operations, methods, and processes described herein are performed by computer system 700 in response to processor(s) 704 executing one or more sequences of one or more instructions contained in main memory 706. Such instructions may be read into main memory 706 from another storage medium, such as storage device 710. Execution of the sequences of instructions contained in main memory 706 may cause processor(s) 704 to perform the process steps described herein. In alternative embodiments, hard-wired circuitry may be used in place of or in combination with software instructions.

The main memory 706, the ROM 708, and/or the storage device 710 may include non-transitory storage media. The term "non-transitory media," and similar terms, as used herein refers to media that store data and/or instructions that cause a machine to operate in a specific fashion, the media excludes transitory signals. Such non-transitory media may comprise non-volatile media and/or volatile media. Non-volatile media includes, for example, optical or magnetic disks, such as storage device 710. Volatile media includes dynamic memory, such as main memory 706. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

The computer system 700 may include a network interface 718 coupled to bus 702. Network interface 718 may provide a two-way data communication coupling to one or more network links that are connected to one or more local networks. For example, network interface 718 may be an integrated services digital network (ISDN) card, cable modem, satellite modem, or a modem to provide a data communication connection to a corresponding type of telephone line. As another example, network interface 718 may be a local area network (LAN) card to provide a data communication connection to a compatible LAN (or WAN component to communicated with a WAN). Wireless links may also be implemented. In any such implementation, network interface 718 may send and receive electrical, electromagnetic or optical signals that carry digital data streams representing various types of information.

The computer system 700 can send messages and receive data, including program code, through the network(s), network link and network interface 718. In the Internet example, a server might transmit a requested code for an application program through the Internet, the ISP, the local network and the network interface 718.

The received code may be executed by processor(s) 704 as it is received, and/or stored in storage device 710, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another or may be combined in various ways. All possible combinations and sub-combinations are intended to fall within the scope of this specification. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The examples of blocks or states may be performed in serial, in parallel, or in some other manner. Blocks or states may be added to or removed from the disclosed embodiments. The examples of systems and components described herein may be configured differently than described. For example, elements may be added to, removed from, or rearranged compared to the disclosed embodiments.

The various operations of methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some embodiments, the processors or processor-implemented engines may be located in a single geographic location (e.g., within a home environment, an office environment, or a server farm). In other embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific embodiments, various modifications and changes may be made to these embodiments without departing from the broader scope of embodiments of the specification. The Detailed Description should not to be taken in a limiting sense, and the scope of various embodiments is defined only by the appended claims, along with the full range of equivalents to which such claims are entitled. Furthermore, related terms (such as "first," "second," "third," etc.) used herein do not denote any order, height, or importance, but rather are used to distinguish one element from another element. Furthermore, the terms "a," "an," and "plurality" do not denote a limitation of quantity herein, but rather denote the presence of at least one of the articles mentioned.

The invention claimed is:

1. A non-transitory computer-readable storage medium with instructions stored thereon, that are executable by one or more processors to cause the one or more processors to perform operations for imaging blood vessels in a region of interest in a patient's body, the operations comprising:

triggering an ultrasound transducer to emit ultrasound waves towards the region of interest;

obtaining via the ultrasound transducer, for each location of multiple locations in the region of interest, a time-dependent ultrasound signal reflected from the region of interest during a time period;

determining, for the each location, an intensity threshold by multiplying a peak value with a percentage threshold, wherein the peak value is a maximum intensity of the time-dependent ultrasound signal during the time period, wherein the percentage threshold is same across the multiple locations, and wherein an intensity threshold of a first location of the multiple locations is different from an intensity threshold of a second location of the multiple locations;

measuring, for the each location, a relative time instant that the obtained time-dependent ultrasound signal reaches the intensity threshold;

comparing a predetermined relative time instant with the measured relative time instant of the each location to determine one or more locations showing abnormality;

resolving tissue boundaries or small blood vessels of vascular structures that are unresolvable by B-mode imaging;

generating an image of the vascular structures on a display by color-coding a structural image of the region of interest based at least on the measured relative time instant of the each location, wherein the generated image of the vascular structures is a color-coded two-dimensional image that displays in different colors and at different time instants corresponding to different locations in the region of interest and shows boundaries of the blood vessels; and labelling the one or more locations showing abnormality on the generated image of the vascular structures.

2. The non-transitory computer-readable storage medium of claim 1, wherein:

the blood vessels in the region of interest have a plurality of different sizes; and the different time instants indicate different blood perfusion rates in the blood vessels.

3. The non-transitory computer-readable storage medium of claim 1, wherein the operations further comprise:

obtaining, for the each location, an updated intensity threshold; and updating the generated image of vascular structures based at least on the updated intensity threshold of the each location.

4. The non-transitory computer-readable storage medium of claim 1, wherein the operations further comprise:

obtaining a window size for image smoothing; and applying a smoothing function on the generated image of the vascular structures based at least on the window size.

5. The non-transitory computer-readable storage medium of claim 1, wherein before the obtaining via the ultrasound transducer, for each location of multiple locations in the region of interest, a time-dependent ultrasound signal reflected from the region of interest during a time period, the operations further comprise:

obtaining a user-input of an end of the time period.

6. A system for imaging blood vessels in a region of interest in a patient's body, comprising:

a computing system;

a data storage;

a display; and an ultrasound transducer coupled to the computing system and the data storage; and wherein the computing system comprising: one or more processors, and one or more non-transitory computer-readable storage media coupled to the one or more processors and having instructions stored thereon that are executable by the one or more processors to cause the one or more processors to perform operations comprising:

triggering the ultrasound transducer to emit ultrasound waves towards the region of interest;

storing in the data storage, for each location of multiple locations in the region of interest, a time-dependent ultrasound signal reflected from the region of interest during a time period;

determining, for the each location, an intensity threshold by multiplying a peak value with a percentage threshold, wherein the peak value is a maximum intensity of the time-dependent ultrasound signal during the time period, wherein the percentage threshold is same across the multiple locations, and wherein an intensity threshold of a first location of the multiple locations is different from an intensity threshold of a second location of the multiple locations;

measuring, for the each location, a relative time instant that the time-dependent ultrasound signal reaches the intensity threshold;

comparing a predetermined relative time instant with the measured relative time instant of the each location to determine one or more locations showing abnormality;

resolving tissue boundaries or small blood vessels of vascular structures that are unresolvable by B-mode imaging;

generating an image of the vascular structures on the display by color-coding a structural image of the region of interest based at least on the measured relative time instant of the each location, wherein the generated image of the vascular structures is a color-coded two-dimensional image that displays in different colors and at different time instants corresponding to different locations in the region of interest and shows boundaries of the blood vessels; and labelling the one or more locations showing abnormality on the generated image of the vascular structures.

7. The system of claim 6, wherein the operations further comprise:

obtaining a window size for image smoothing; and applying a smoothing function on the generated image of the vascular structures based at least on the window size.

8. The system of claim 6, wherein:

the blood vessels in the region of interest have a plurality of different sizes; and the different time instants indicate different blood perfusion rates in the plurality of blood vessels.

9. The system of claim 6, wherein the operations further comprise:

obtaining, for the each location, an updated intensity threshold; and updating the generated image of vascular structures based at least on the updated intensity threshold of the each location.

10. The system of claim 6, wherein before the storing in the data storage, for each location of multiple locations in the region of interest, a time-dependent ultrasound signal reflected from the region of interest during a time period, the operations further comprise:

obtaining a user-input of an end of the time period.

11. A method of imaging blood vessels in a region of interest in a patient's body, comprising:

administering to the patient an ultrasound contrast agent through vascular injection;

emitting an ultrasound wave towards the region of interest;

obtaining, for each location of multiple locations in the region of interest, a time-dependent ultrasound signal reflected from the region of interest during a time period;

determining, for the each location, an intensity threshold by multiplying a peak value with a percentage threshold, wherein the peak value is a maximum intensity of the time-dependent ultrasound signal during the time period, wherein the percentage threshold is same across the multiple locations, and wherein an intensity threshold of a first location of the multiple locations is different from an intensity threshold of a second location of the multiple locations;

measuring, for the each location, a relative time instant that the obtained time-dependent ultrasound signal reaches the intensity threshold;

comparing a predetermined relative time instant with the measured relative time instant of the each location to determine one or more locations showing abnormality;

resolving tissue boundaries or small blood vessels of vascular structures that are unresolvable by B-mode imaging;

generating an image of the vascular structures by color-coding a structural image of the region of interest based at least on the measured relative time instant of the each location, wherein the generated image of the vascular structures is a color-coded two-dimensional image that displays in different colors and at different time instants corresponding to different locations in the region of interest and shows boundaries of the blood vessels; and labelling the one or more locations showing abnormality on the generated image of the vascular structures.

12. The method of claim 11, wherein the method further comprises:

obtaining a window size for image smoothing; and applying a smoothing function on the generated image of the vascular structures.

13. The method of claim 11, wherein:

the blood vessels in the region of interest have a plurality of different sizes; and the different time instants indicate different blood perfusion rates in the blood vessels.

14. The method of claim 11, wherein the method further comprises:

obtaining, for the each location, an updated intensity threshold; and updating the generated image of vascular structures based at least on the updated intensity threshold of the each location.

* * * * *